US00PP21045P2

(12) United States Plant Patent

Burr et al.

(10) Patent No.: US PP21,045 P2

(45) Date of Patent: Jun. 1, 2010

(54) HYBRID VARIETY OF TEXAS×KENTUCKY BLUEGRASS DESIGNATED 'HB 128'

(50) Latin Name: ***Poa arachnifera Torr.×Poa pratensis* L.**

Varietal Denomination: HB 128

(75) Inventors: Jay B. Burr, Salem, OR (US); George Marquez, Turner, OR (US); James R. Frelich, Salem, OR (US); John R. Hardison, Corvallis, OR (US)

(73) Assignee: SMG Brands, Inc., Wilmington, DE (US)

( * ) Notice: Subject to any disclaimer, the term of this patent is extended or adjusted under 35 U.S.C. 154(b) by 99 days.

(21) Appl. No.: 12/071,554

(22) Filed: Feb. 22, 2008

(51) Int. Cl.
*A01H 5/00* (2006.01)

(52) U.S. Cl. ..... Plt./393

(58) Field of Classification Search ..... Plt./393
See application file for complete search history.

(56) References Cited

U.S. PATENT DOCUMENTS

| | | | |
|---|---|---|---|
| PP3,156 | P | 7/1970 | Fuchigami et al. |
| PP3,150 | P | 5/1972 | Pepin et al. |
| PP3,186 | P | 5/1972 | Barenbrug et al. |
| PP4,336 | P | 11/1978 | Mayer et al. |
| PP6,280 | P | 9/1988 | Meier et al. |
| PP6,537 | P | 1/1989 | Meier et al. |
| PP6,538 | P | 1/1989 | Meier et al. |
| PP6,585 | P | 2/1989 | Meier et al. |
| PP7,831 | P | 3/1992 | Meier et al. |
| PP8,490 | P | 12/1993 | Meier et al. |
| PP9,036 | P | 1/1995 | Meier et al. |
| PP9,209 | P | 7/1995 | Meier et al. |
| PP9,611 | P | 7/1996 | Meier |
| PP9,848 | P | 4/1997 | Meier et al. |
| PP9,977 | P | 7/1997 | Meier et al. |
| PP10,080 | P | 10/1997 | Meier et al. |
| PP10,081 | P | 10/1997 | Meier et al. |
| PP10,384 | P | 5/1998 | Meier et al. |
| PP10,925 | P | 5/1999 | Meier et al. |
| PP11,520 | P | 9/2000 | Meier et al. |
| PP11,536 | P | 10/2000 | Meier et al. |
| PP12,435 | P2 | 3/2002 | Meier et al. |
| PP18,439 | P2 | 1/2008 | Hardison et al. |
| PP18,467 | P2 | 1/2008 | Hardison et al. |

OTHER PUBLICATIONS

Drought resistance of two texas Bluegrass hybrids compared with kentucky Bluegrass and Tall Fescue. Bremer d. et al. K-State Turfgrass Research. Report of Progress 911. 2003. p. 67-44.

Agronomy J., 41(8):393-394; Aug. 1949.

Alderson et al., Grass Varieties in the United States, U.S. Dept. of Agriculture, Handbook No. 170:233-234; 1994.

Beard et al., Beard's Turfgrass Encyclopedia for Gold Courses Grounds Lawns Sports Fields, definitions of apomixis, p. 23; 2005.

Bulletin of the Agricultural Experiment Station of the University of Tennessee, The Grasses of Tennessee—Part I, V(2):29, 45, 60-63, 94-97; Apr. 1892.

Curley et al., RAPD-Based Genetic Relationships in Kentucky Bluegrass: Comparison of Cultivars, Interspecific Hybrids, and Plant Introductions, reproduced from Crop Sci. 44:1299-1306; 2004.

Lamson-Scibner, American Grasses-II (Illustrated), U.S. Dept. of Agriculture, Bulletin No. 17:246;1899.

Manual for Testing Agricultural and Vegetable Seeds, Agriculture Handbook, No. 30: 67-70, 224-227; 396-397, Plates VIII-X; 1952.

Piper, Blue Grasses, Meadow-Grasses and Redtop in Forage Plants and Their Culture, pp. 155-171; 1919.

Porceddu et al. Linkage Mapping in apomictic and sexual Kentucky bluegrass (*Poa pratensis* L.) genotypes using a two way pseudo-testcross strategy based on AFLP and SAMPL markers, Theor Appl Genet, Feb. 2004; 104(2-3):273-280.

Read et al., Registration of 'Reveille' Hybrid Bluegrass, Crop Science, 39:590; Mar.-Apr. 1999.

Read et al., Texas Bluegrass (*Poa arachnifera* Torr.) in Turfgrass Biology, Genetics, and Bredding, Casler and Duncan, eds., pp. 61-66; 2003.

Silveus et al., Texas Grasses, Classification and Description of Grass, Descriptive Systematic Agrostology, Introduction-Illustrations XV-XVII, pp. 33-48; 1933.

Yearbook of Agriculture, U.S. Dept. of Agriculture, 75$^{th}$ Congress, 1$^{st}$ Session, House Document No. 28:1056-1070; 1937.

Yearbook of the U.S. Dept. of Agriculture, pp. 139, 145-146, Plates IV-V; 1908.

*Primary Examiner*—June Hwu

(74) *Attorney, Agent, or Firm*—Hunton & Williams LLP

(57) ABSTRACT

A hybrid variety of Texas bluegrass×Kentucky bluegrass as described, characterized by rapid establishment; a medium dark green, dense turf; a medium wide leaf blade; aggressive spreading growth; a reduced level of cotton on the seed; and a medium to high seed yield potential.

3 Drawing Sheets

BACKGROUND OF THE INVENTION (a) Field of the Invention

The present invention relates to a new and distinct hybrid variety of *Poa arachnifera* Torr.×*Poa pratensis* L. that has been designated as 'HB 128' bluegrass.

(b) Description of Related Art

A *Poa arachnifera*×*Poa pratensis* hybrid designated 'HB 129' bluegrass having the same female parents as those employed in breeding the present 'HB 128' bluegrass has been disclosed in U.S. Plant Pat. No. 18,467, issued Jan. 29, 2008. Also, a *Poa arachnifera*×*Poa pratensis* hybrid designated 'Reveille' has been disclosed in PVP Certificate No. 9800337.

SUMMARY OF THE VARIETY

'HB 128' bluegrass is the result of a single plant selected from the progeny of Texas bluegrass (*Poa arachnifera* Torr.)

female plant '10-10' (seed parent), with cv. 'Geronimo' Kentucky bluegrass (pollen parent)(*Poa pratensis* L.) cross for perfect flowers, apomixis and turfgrass performance characteristics in the $F_1$ generation.

Texas bluegrass female plant '10-10' is an unpatented, unreleased plant selected and maintained for its tiller density, turf quality and the lack of male reproductive organs. The cv. 'Geronimo' is an unpatented, released Kentucky bluegrass of European origin from Mommersteeg International, Vlijmen, the Netherlands. 'HB 128' morphologically possesses both female and male bearing structures (pistils and stamens), whereas the female parent '10-10' morphologically possesses only female bearing structures (pistils) and is void of male flowering structures (stamens).

Although the 'HB 128' and 'HB 129' are derived from the same parent plants, genetic variations between these species are virtually inevitable. During sexual reproduction, the genome of each parent divides resulting in two different genomes for both the female Texas bluegrass parent and two different genomes for the male parent 'Geronimo'. Therefore, during the cross, four different combinations are possible. In addition, Geronimo is composed of a number of strains. See Grass Varieties of The United States, Handbook No. 110 rev, 1994, page 233 and the description of 'Geronimo' under the "Method of Breeding" section, which is incorporated by reference herein. Thus, even though the parents are the same, progeny are not going to receive the same set of genomes; the result is genomes that are split and unaligned.

As a result of this breeding, a distinct variety was selected, produced and asexually propagated by rhizomes, tillers and disseminules. The highly apomictic seed of 'HB 128' bluegrass was produced first at Gervais, Oreg. This seed was used to plant turf performance evaluation trials and later, seed production fields.

The seed of 'HB 128' has been found to be stable. Asexual production of 'HB 128' initially was performed at Gervais, Oreg. by propagules (tillers and rhizomes) and by disseminules (modified caryopses produced by apomixis), and has consistently produced progeny plants indistinguishable from the first generation asexual reproductions of the instant plant. The apomixis level of 'HB128' is approximately 99.0%. The apomixis level was determined by examining field planting of 'HB 128' in one year of rating for apomictic origin and from disseminules harvested over four growing seasons from field grown plants in Oregon.

'HB 128' has a number of highly desirable characteristics, including a high level of seedling vigor and rapid stand establishment. 'HB 128' has an upright leafy turf type, medium leaf texture, a medium dark green color, and less than average leaf glaucosity which can be maintained throughout the entire growing season. 'HB 128' demonstrates early spring greenup and growth under mild winter conditions. 'HB 128' has an aggressive, spreading habit.

'HB 128' has a medium to high seed yield potential in the Kentucky bluegrass seed production region of the northwestern United States and has shown the potential for economic seed production not seen in other *Poa arachnifera*×*Poa pratensis* hybrids.

In comparison with the 'Reveille' hybrid, 'HB 128' has demonstrated relatively rapid germination and emergence in fall sowings. In comparison with 'HB 129', 'HB 128' is a darker green color, shows better tolerance to foliar disease, is quicker to spring greenup and has a more rapid germination and establishment.

Texas bluegrass is a vigorous sod-forming perennial native in the Southeastern and Southern Plains States. Plants grow up to 3 feet on strong soil, with numerous leaves 6 to 12 inches long and 0.025 inch wide. The grass grows throughout the winter producing abundant, nutritious pasture which is highly palatable. This is a valuable species where native, but seeding is difficult. The species is dioecious, with male and female plants. It produces only limited quantities of seed which is covered with woolly hairs that are difficult to remove. Consequently, establishment of stands for agricultural use is limited. Accordingly, Texas bluegrass exhibits similar problems to those encountered with Reveille which are overcome by the present 'HB 128' hybrid.

DETAILED DESCRIPTION OF THE VARIETY

Figure 1:
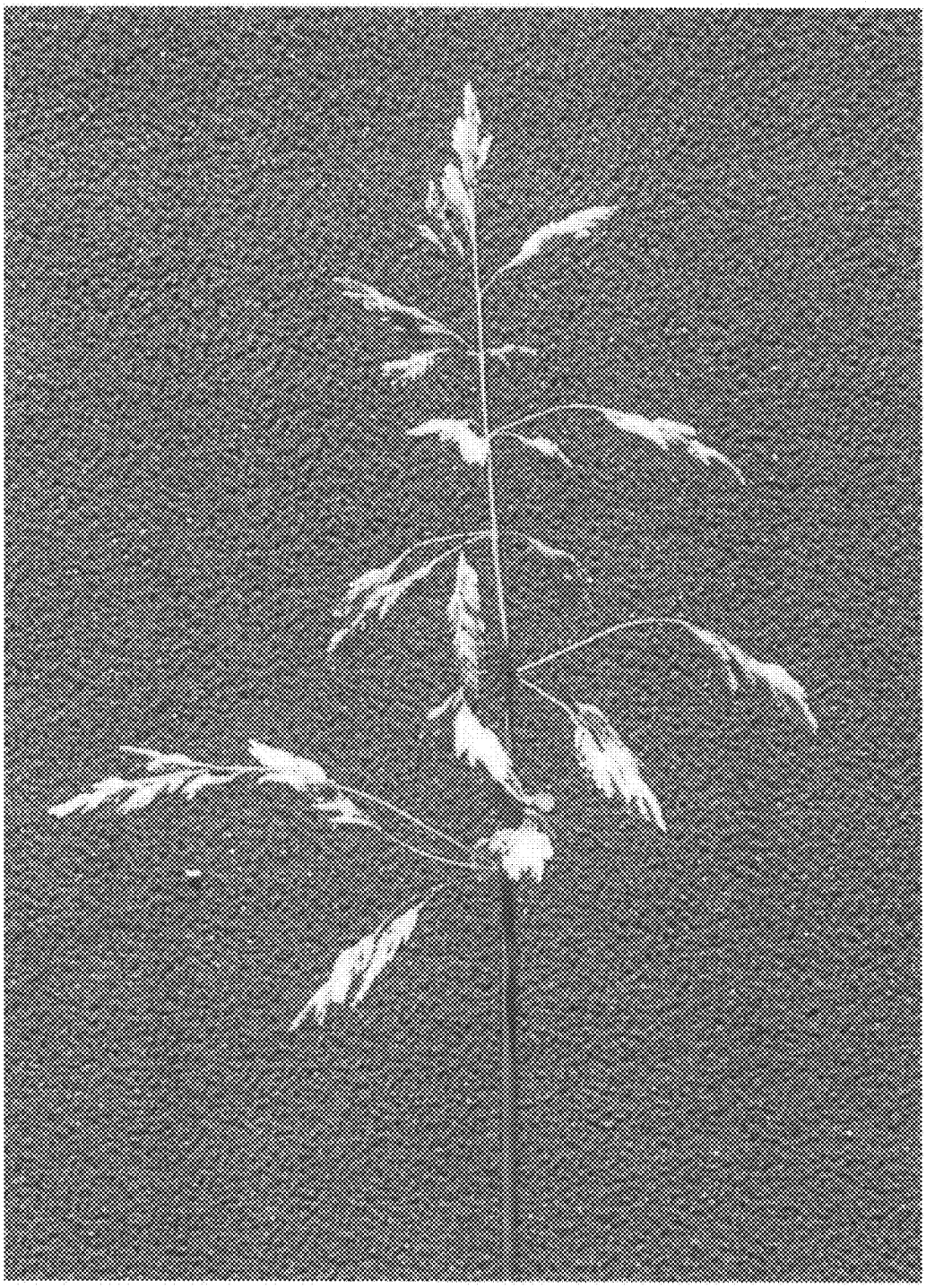
FIG. 1 is an 'HB 128' panicle.
Figure 2:
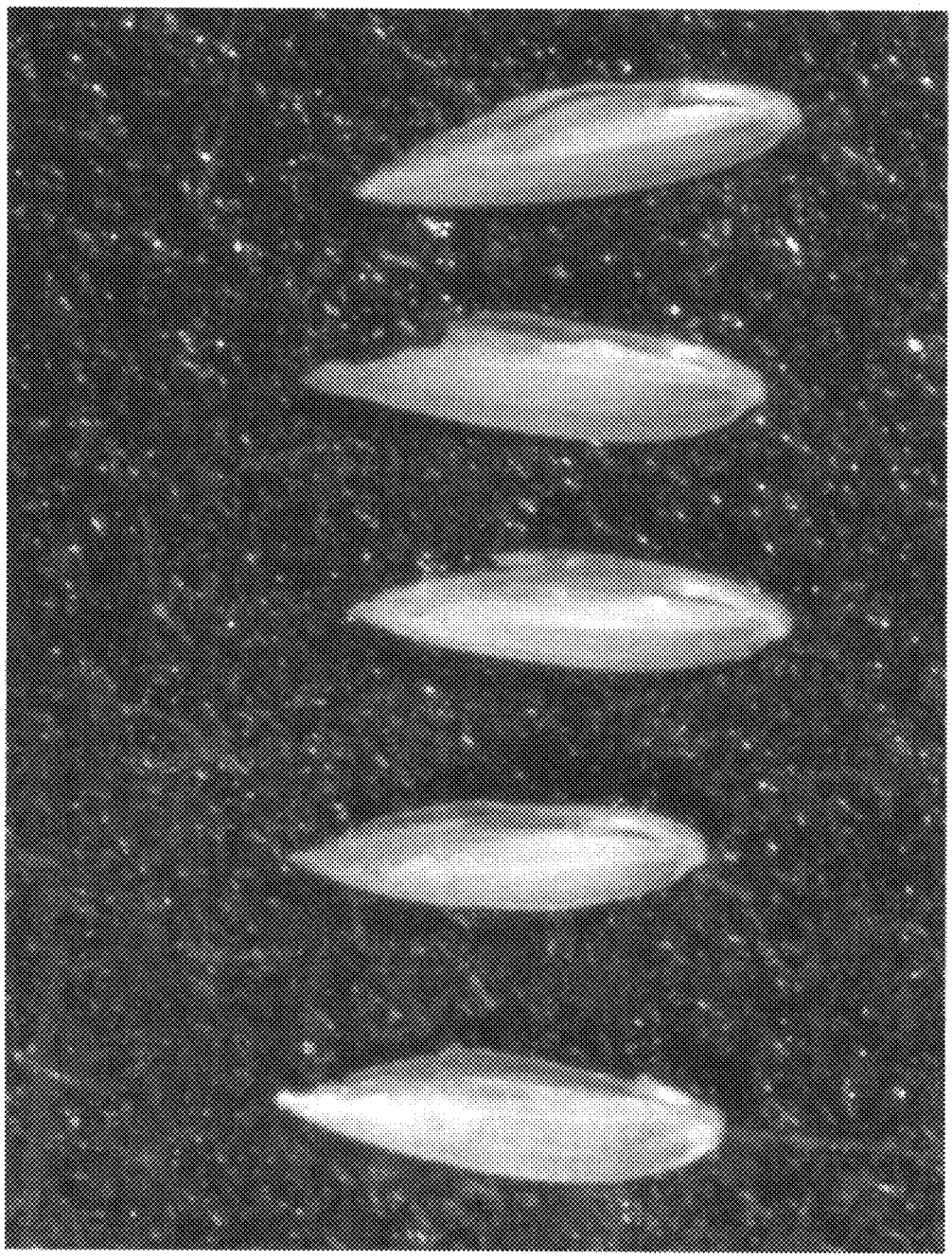
FIG. 2 is an 'HB 128' seed.
Figure 3:
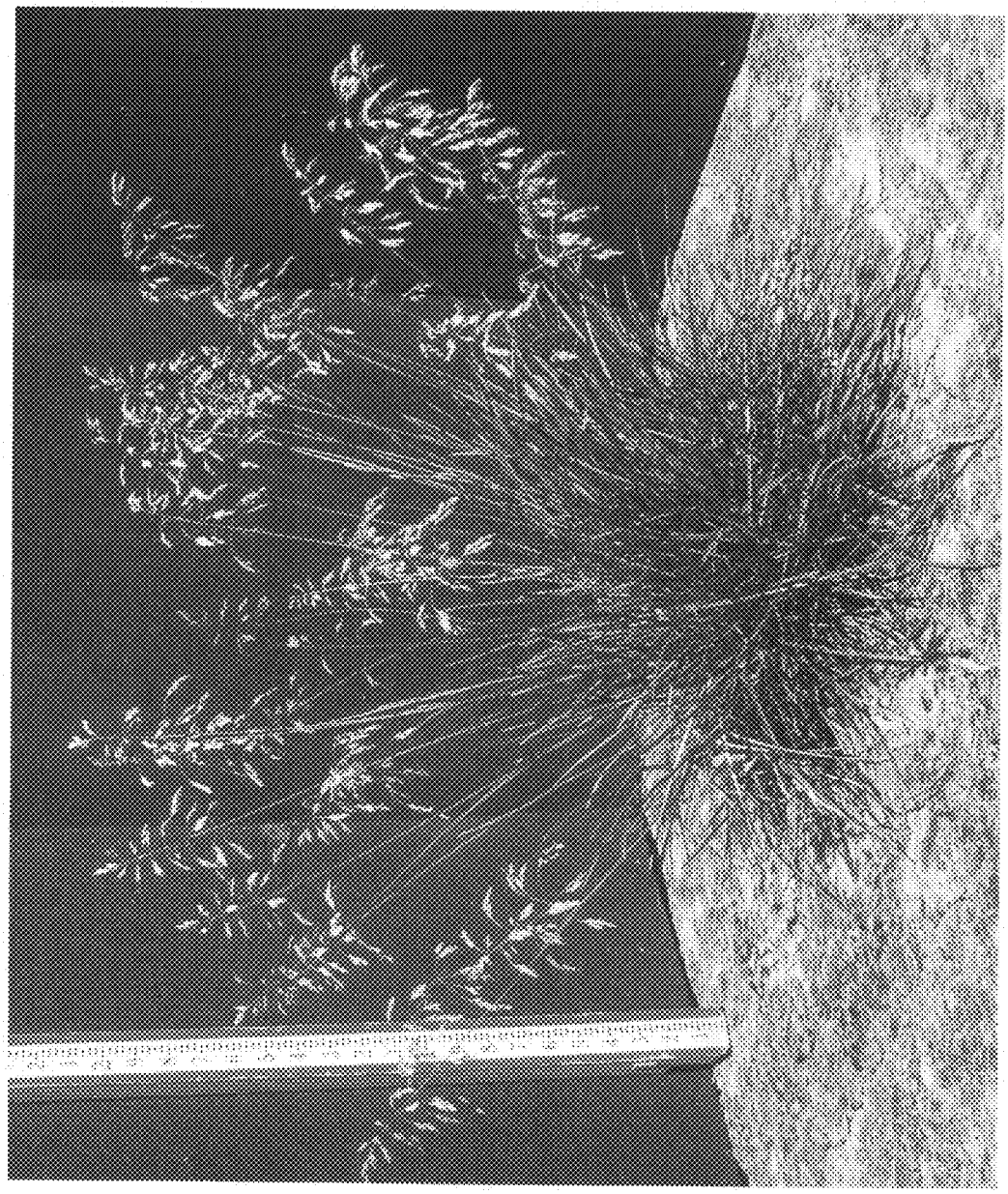
FIG. 3 is an 'HB 128' plant shortly after completing anthesis.

'HB 128' Texas bluegrass×Kentucky bluegrass (*Poa arachnifera* L.×*Poa pratensis* L.) hybrid is perennial with creeping rhizomes forming a dense turf. When plants grown over winter in the field and grown undisturbed by clipping, the culms are semi-erect averaging 62.6 cm in length. See Table 7 below. The vegetative leaf averages 8.6 cm in length. See Table 16 below. Flag leaf length averages 5.65 cm in length, 4.4 mm in width and has a sheath length of 13.4 cm. See Tables 19, 20 and 23 below. The flag leaf ligule averages 1.9 mm in length and has more than average hairs on ligule than other varieties. See Table 30 below. The panicle averages 10.1 cm in length and 10.3 cm in width. See Tables 34 and 35 below. The lowest whorl of the panicle averages 4.4 branches, the third whorl averages 3.7 branches, and the peduncle averages 30.4 cm in length. See Tables 42, 48 and 49 below.

'HB 128' produces inflorescences relatively early compared with Kentucky bluegrasses.

Comparisons of 'HB 128' were made with other hybrid bluegrass varieties as well as Texas and Kentucky bluegrasses in three nurseries (designated #1–#3) in Gervais, Oreg. See Tables 1–60 below. Each nursery contained a different soil type (e.g., having different pHs) and were planted in different years.

Comparisons of 'HB 128' were also made with various Kentucky bluegrasses in turf plantings in California, Oregon and Texas. See Tables 61–66 below.

TABLE 1

Comparison of heading dates (Julian) of 'HB-128' and Kentucky and Texas bluegrass cultivars planted in nursery #3.

| Variety | Growing Season #1 | Growing Season #2 |
|---|---|---|
| 'HB-128' | 133.2 | 119.1 |
| 'HB-129' | 133.4 | 119.6 |
| 'HB-130' | 133.1 | 119.4 |
| 'HB-328' | 135.4 | 118.3 |
| 'HB-329' | 135.6 | 116.1 |
| 'Geronimo' | 127.6 | 119.4 |
| 'TX51-90' | 127.1 | 93.0 |
| 'TX49-90' | 123.7 | 106.1 |
| 'Ascot' | 135.8 | 124.7 |
| 'Midnight' | 143.3 | 137.0 |
| 'Reveille' | 130.8 | 111.8 |

TABLE 1-continued

Comparison of heading dates (Julian) of 'HB-128' and Kentucky and Texas bluegrass cultivars planted in nursery #3.

| Variety | Growing Season #1 | Growing Season #2 |
|---|---|---|
| 'Kelly' | 138.7 | 128.0 |
| LSD (P = .05) | 4.0 | 4.2 |

TABLE 2

Comparison of heading dates (Julian) of 'HB-128' and Kentucky and Texas bluegrass cultivars planted in nursery #1.

| Variety | Growing Season #1 | Growing Season #2 |
|---|---|---|
| 'HB-128' | 105.7 | 114.0 |
| 'HB-129' | 108.0 | 115.0 |
| 'HB-130' | 105.0 | 115.0 |
| 'Abbey' | 108.3 | 112.7 |
| 'HB 329' | 114.3 | 105.0 |
| 'Ascot' | 109.7 | 113.3 |
| 'Geronimo' | 105.0 | 114.0 |
| 'TX 19-88' | 119.5 | 94.5 |
| 'TX 46-90' | 113.0 | 94.0 |
| TX 4-88' | 103.0 | 94.0 |
| LSD (P = .05) | 5.6 | 3.4 |

TABLE 3

Comparison of anthesis dates (Julian) of 'HB-128' and Kentucky and Texas bluegrass cultivars planted in nursery #3.

| Variety | Growing Season #1 | Growing Season #2 |
|---|---|---|
| 'HB-128' | 138.9 | 132.3 |
| 'HB-129' | 138.4 | 132.2 |
| 'HB-130' | 140.8 | 132.6 |
| 'HB-328' | 143.5 | 134.8 |
| 'HB-329' | 142.7 | 131.2 |
| 'Geronimo' | 136.5 | 133.6 |
| 'TX51-90' | 138.5 | 124.8 |
| 'TX49-90' | 139.0 | 128.3 |
| 'Ascot' | 141.1 | 134.3 |
| 'Midnight' | 148.7 | 143.5 |
| 'Reveille' | 146.4 | 135.3 |
| 'Kelly' | 145.5 | 137.4 |
| LSD (P = .05) | 3.6 | 3.3 |

TABLE 4

Comparison of heading and anthesis dates (Julian) of 'HB-128' and Kentucky and Texas bluegrass cultivars planted in nursery #2.

| Variety | Heading Date | Anthesis Date |
|---|---|---|
| 'HB-128' | 122.0 | 138.3 |
| 'HB-129' | 119.5 | 138.0 |
| 'HB-130' | 121.5 | 140.8 |
| 'HB-328' | 118.4 | 135.6 |
| 'HB 329' | 123.0 | 144.8 |
| 'Reveille' | 115.8 | 141.4 |
| Geronimo' | 121.6 | 139.9 |
| 'Ascot' | 123.7 | 140.5 |
| "Midnight | 142.3 | 148.2 |
| 'Buckingham' | 124.5 | 141.8 |
| 'TX 51-91' | 116.2 | 139.7 |
| 'TX 39-88' | 121.4 | |
| TX 49-90' | 119.2 | 139.5 |
| 'Kelly' | 130.8 | 143.4 |
| LSD (p = .05) | 4.7 | 5.0 |

TABLE 5

Comparison of Anther Color of 'HB-128' and Kentucky and Texas bluegrass cultivars planted in nursery #3.
(1 = Purple, 2 = Yellow, 3 = Brown, 4 = Blue, and 5 = Black)

| Variety | Growing Season #1 | Growing Season #2 |
|---|---|---|
| 'HB-128' | 1.8 | 1.3 |
| 'HB-129' | 1.8 | 2.1 |
| 'HB-130' | 1.6 | 1.9 |
| 'HB-328' | 1.8 | 3.4 |
| 'HB-329' | 1.8 | 2.4 |
| 'Geronimo' | 1.4 | 2.0 |
| 'TX51-90' | 2.0 | 2.0 |
| 'TX49-90' | 2.0 | 1.9 |
| 'Ascot' | 1.6 | 3.2 |
| 'Midnight' | 1.0 | 2.0 |
| 'Reveille' | 1.8 | 2.0 |
| 'Kelly' | 1.7 | 2.9 |
| LSD (p = .05) | 0.4 | 1.3 |

TABLE 6

Comparison of field plant height (cm) of 'HB-128' and Kentucky and Texas bluegrass cultivars grown in nursery #3.

| Variety | Growing Season #1 | Growing Season #2 |
|---|---|---|
| 'HB-128' | 54.6 | 57.4 |
| 'HB-129' | 57.2 | 58.1 |
| 'HB-130' | 54.9 | 57.3 |
| 'HB-328' | 36.7 | 41.0 |
| 'HB-329' | 37.9 | 46.0 |
| 'Geronimo' | 54.7 | 59.5 |
| 'TX51-90' | 49.6 | 71.2 |
| 'TX49-90' | 46.9 | 69.7 |
| 'Ascot' | 32.0 | 30.7 |
| 'Midnight' | 36.6 | |
| 'Reveille' | 54.9 | 71.9 |
| 'Kelly' | 43.0 | 27.2 |
| LSD (P = .05) | 6.5 | 7.0 |

TABLE 7

Comparison of length of harvested culms of 'HB-128' and Kentucky and Texas bluegrass cultivars planted in nursery #3.

| | Culm Length (cm) | |
|---|---|---|
| Variety | Growing Season #1 | Growing Season #2 |
| 'HB-128' | 61.2 | 64.1 |
| 'HB-129' | 62.6 | 62.9 |
| 'HB-130' | 61.0 | 64.4 |
| 'HB-328' | 44.9 | 62.4 |
| 'HB-329' | 36.1 | 58.9 |
| 'Geronimo' | 58.5 | 56.5 |
| 'TX51-90' | 55.9 | 72.4 |
| 'TX49-90' | 49.8 | 74.7 |
| 'Ascot' | 42.7 | 49.9 |
| 'Midnight' | 47.1 | 54.6 |
| 'Reveille' | 62.3 | 74.3 |
| 'Kelly' | 48.9 | 54.9 |
| LSD (P = .05) | 5.4 | 5.4 |

TABLE 8

Comparison plant height in the field and the height of harvested culms of 'HB-128' and Kentucky and Texas bluegrass cultivars planted in nursery #2.

| Variety | Plant Height - Field (cm) | Height of Harvested Culms (cm) |
|---|---|---|
| 'HB-128' | 54.5 | 58.5 |
| 'HB-129' | 58.3 | 64.8 |
| 'HB-130' | 54.6 | 63.0 |
| 'HB-328' | 40.4 | 55.7 |
| 'HB 329' | 35.8 | 49.5 |
| 'Reveille' | 51.6 | 62.6 |
| Geronimo' | 56.9 | 67.6 |
| 'Ascot' | 38.2 | 52.4 |
| 'Midnight' | 29.7 | 51.8 |
| 'Buckingham' | 48.2 | 62.4 |
| 'TX 51-91' | 44.5 | 49.1 |
| 'TX 39-88' | 56.8 | 56.8 |
| TX 49-90' | 52.6 | 63.7 |
| 'Kelly' | 38.0 | 54.9 |
| LSD (P = .05) | 8.4 | 7.2 |

TABLE 9

Comparison of the Distance (cm) from Basil Node to Tiller Leaf Node of 'HB-128' and Kentucky and Texas bluegrass cultivars planted in nursery #3.

| Variety | Growing Season #1 | Growing Season #2 |
|---|---|---|
| 'HB-128' | 5.7 | 10.3 |
| 'HB-129' | 6.1 | 9.5 |
| 'HB-130' | 5.8 | 8.7 |
| 'HB-328' | 3.6 | 9.0 |
| 'HB-329' | 2.1 | 3.8 |
| 'Geronimo' | 4.9 | 9.7 |
| 'TX51-90' | 0.5 | 3.1 |
| 'TX49-90' | 1.0 | 3.6 |
| 'Ascot' | 2.9 | 4.8 |
| 'Midnight' | 5.3 | 9.3 |
| 'Reveille' | 1.8 | 4.7 |
| 'Kelly' | 4.4 | 6.6 |
| LSD (P = .05) | 1.4 | 2.4 |

TABLE 10

Comparison of the distance (cm) from basal node to the flag leaf node for 'HB-128' and Kentucky and Texas bluegrass cultivars planted in nursery #3.

| Variety | Growing Season #1 | Growing Season #2 |
|---|---|---|
| 'HB-128' | 17.2 | 26.3 |
| 'HB-129' | 21.4 | 23.7 |
| 'HB-130' | 18.7 | 24.1 |
| 'HB-328' | 11.9 | 22.8 |
| 'HB-329' | 8.5 | 16.0 |
| 'Geronimo' | 16.3 | 22.7 |
| 'TX51-90' | 5.2 | 13.9 |
| 'TX49-90' | 8.3 | 19.5 |
| 'Ascot' | 10.5 | 11.7 |
| 'Midnight' | 8.4 | 19.0 |
| 'Reveille' | 12.2 | 21.1 |
| 'Kelly' | 13.1 | 16.2 |
| LSD (p = .05) | 3.6 | 5.0 |

TABLE 11

Comparison of the number of nodes on flowering culms of 'HB-128' and Kentucky and Texas bluegrass cultivars planted in nursery #3.

| Variety | Growing Season #1 | Growing Season #2 |
|---|---|---|
| 'HB-128' | 4.1 | 5.5 |
| 'HB-129' | 4.3 | 4.9 |
| 'HB-130' | 4.3 | 4.9 |
| 'HB-328' | 3.7 | 5.0 |
| 'HB-329' | 3.0 | 4.6 |
| 'Geronimo' | 4.8 | 5.5 |
| 'TX51-90' | 2.3 | 3.8 |
| 'TX49-90' | 2.4 | 3.5 |
| 'Ascot' | 3.7 | 4.8 |
| 'Midnight' | 4.5 | 5.9 |
| 'Reveille' | 3.2 | 3.1 |
| 'Kelly' | 4.2 | 5.1 |
| LSD (p = .05) | 0.7 | 0.7 |

TABLE 12

Comparison of the number of nodes on flowering culm for 'HB-128' and Kentucky and Texas bluegrass cultivars planted at nursery #2.

| Variety | Growing Season |
|---|---|
| 'HB-128' | 4.1 |
| 'HB-129' | 4.5 |
| 'HB-130' | 4.4 |
| 'HB-328' | 3.0 |
| 'HB 329' | 3.1 |
| 'Reveille' | 2.8 |
| Geronimo' | 4.7 |
| 'Ascot' | 4.1 |
| 'Midnight' | 4.5 |
| 'Buckingham' | 4.6 |
| 'TX 51-91' | 2.2 |
| 'TX 39-88' | 2.1 |
| TX 49-90' | 2.4 |
| 'Kelly' | 4.1 |
| LSD (P = .05) | 1.1 |

TABLE 13

Comparison of the number of nodes on flowering culms for 'HB-128' and Kentucky and Texas bluegrass cultivars planted in nursery #1.

| Variety | Growing Season |
|---|---|
| 'HB-128' | 4.9 |
| 'HB-129' | 4.7 |
| 'HB-130' | 3.9 |
| 'Abbey' | 4.1 |
| 'HB 329' | 4.2 |
| 'Ascot' | 4.8 |
| 'Geronimo' | 4.1 |
| 'TX 19-88' | 3.8 |
| 'TX 46-90' | 3.4 |
| TX 4-88' | 4.1 |
| LSD (p = .05) | 0.9 |

TABLE 14

Comparison of plant growth habit of 'HB-128' and Kentucky and Texas bluegrass cultivars planted in nursery #3. (1 = Prostrate, 2 = Semi-prostrate, 3 = Erect growth habit).

| Variety | Growing Season |
|---|---|
| 'HB-128' | 1.93 |
| 'HB-129' | 2.00 |
| 'HB-130' | 2.00 |
| 'HB-328' | 1.07 |
| 'HB-329' | 2.00 |
| 'Geronimo' | 1.67 |
| 'TX51-90' | 3.00 |
| 'TX49-90' | 3.00 |
| 'Ascot' | 1.00 |
| 'Midnight' | 1.10 |
| 'Reveille' | 3.00 |
| 'Kelly' | 1.23 |
| LSD (P = .05) | 0.3 |

TABLE 15

Comparison of plant leaf tissue color of 'HB 128' and other bluegrass plants planted in nursery #3 (based on Munsell color charts for plant tissue of hue/value/chroma).

| | ←Lighter Green to Darker Green → | | | |
|---|---|---|---|---|
| Variety | 7.5GY 4/6 | 2.5G 4/4 | 2.5G 4/6 | 5G 4/4 |
| 'HB 128' | 0% | 79% | 14% | 7% |
| 'HB 129' | 47% | 13% | 0% | 40% |
| 'HB 130' | 0% | 57% | 29% | 0% |

*This table shows that 'HB 128' is darker green than 'HB 129' based on color charts.

TABLE 16

Comparison of vegetative leaf length (cm) of 'HB-128' and Kentucky and Texas bluegrass cultivars planted in nursery #3.

| Variety | Growing Season #1 | Growing Season #2 |
|---|---|---|
| 'HB-128' | 8.3 | 8.8 |
| 'HB-129' | 5.5 | 9.3 |
| 'HB-130' | 8.1 | 10.3 |
| 'HB-328' | 7.2 | 10.6 |
| 'HB-329' | 6.5 | 9.7 |
| 'Geronimo' | 8.3 | 9.8 |
| 'TX51-90' | 13.2 | 15.6 |
| 'TX49-90' | 7.9 | 16.6 |
| 'Ascot' | 6.5 | 7.87 |
| 'Midnight' | 8.0 | 11.6 |
| 'Reveille' | 10.7 | 14.0 |
| 'Kelly' | 7.1 | 9.2 |
| LSD (P = .05) | 2.0 | 2.7 |

TABLE 17

Comparison of vegetative leaf length (cm) and width (mm) of 'HB-128' and Kentucky and Texas bluegrass cultivars planted in nursery #2.

| Variety | Vegetative Leaf Length (cm) | Vegetative Leaf Width (mm) |
|---|---|---|
| 'HB-128' | 7.7 | 3.9 |
| 'HB-129' | 9.4 | 4.6 |
| 'HB-130' | 9.0 | 4.6 |
| 'HB-328' | 7.8 | 4.1 |
| 'HB 329' | 9.4 | 4.9 |

TABLE 17-continued

Comparison of vegetative leaf length (cm) and width (mm) of 'HB-128' and Kentucky and Texas bluegrass cultivars planted in nursery #2.

| Variety | Vegetative Leaf Length (cm) | Vegetative Leaf Width (mm) |
|---|---|---|
| 'Reveille' | 9.2 | 3.0 |
| Geronimo' | 9.1 | 4.6 |
| 'Ascot' | 8.6 | 3.7 |
| 'Midnight' | 7.6 | 4.0 |
| 'Buckingham' | 10.2 | 5.1 |
| 'TX 51-91' | 9.1 | 3.6 |
| 'TX 39-88' | 9.0 | 4.6 |
| TX 49-90' | 12.3 | 5.9 |
| 'Kelly' | 9.8 | 3.9 |
| LSD (P = .05) | 3.3 | 1.0 |

TABLE 18

Comparison of flag leaf length (cm) for 'HB-128' and Kentucky and Texas bluegrass cultivars planted in nursery #3.

| Variety | Growing Season #1 | Growing Season #2 |
|---|---|---|
| 'HB-128' | 5.9 | 5.4 |
| 'HB-129' | 5.9 | 5.9 |
| 'HB-130' | 5.8 | 6.7 |
| 'HB-328' | 4.7 | 7.4 |
| 'HB-329' | 5.0 | 6.7 |
| 'Geronimo' | 5.7 | 6.0 |
| 'TX5l-90' | 11.1 | 15.7 |
| 'TX49-90' | 6.8 | 14.0 |
| 'Ascot' | 4.3 | 5.5 |
| 'Midnight' | 5.8 | 8.1 |
| 'Reveille' | 9.5 | 13.1 |
| 'Kelly' | 4.4 | 6.9 |
| LSD (p = .05) | 1.6 | 2.1 |

TABLE 19

Comparison of the flag leaf width (mm) of 'HB-128' and Kentucky and Texas bluegrass cultivars planted in nursery #3.

| Variety | Growing Season #1 | Growing Season #2 |
|---|---|---|
| 'HB-128' | 4.6 | 4.2 |
| 'HB-129' | 4.5 | 4.0 |
| 'HB-130' | 4.6 | 3.3 |
| 'HB-328' | 3.8 | 3.8 |
| 'HB-329' | 4.1 | 3.3 |
| 'Geronimo' | 5.0 | 3.0 |
| 'TX51-90' | 4.9 | 4.5 |
| 'TX49-90' | 5.1 | 4.8 |
| 'Ascot' | 4.0 | 3.6 |
| 'Midnight' | 3.6 | 3.7 |
| 'Reveille' | 4.1 | 3.1 |
| 'Kelly' | 4.2 | 4.0 |
| LSD (P = .05) | 0.6 | 0.8 |

TABLE 20

Flag leaf length (cm) and width (mm) of 'HB-128' and Kentucky and Texas bluegrass cultivars planted in nursery #2.

| Variety | Flag Leaf Length (cm) | Flag Leaf Width (mm) |
|---|---|---|
| 'HB-128' | 5.1 | 3.3 |
| 'HB-129' | 7.2 | 4.0 |
| 'HB-130' | 6.5 | 4.0 |
| 'HB-328' | 6.8 | 3.7 |

TABLE 20-continued

Flag leaf length (cm) and width (mm) of 'HB-128' and Kentucky and Texas bluegrass cultivars planted in nursery #2.

| Variety | Flag Leaf Length (cm) | Flag Leaf Width (mm) |
|---|---|---|
| 'HB 329' | 5.8 | 3.6 |
| 'Reveille' | 7.6 | 3.2 |
| Geronimo' | 6.7 | 4.2 |
| 'Ascot' | 5.9 | 3.2 |
| 'Midnight' | 5.0 | 3.1 |
| 'Buckingham' | 6.2 | 4.2 |
| 'TX 51-91' | 7.3 | 3.8 |
| 'TX 39-88' | 8.1 | 4.6 |
| TX 49-90' | 9.0 | 5.3 |
| 'Kelly' | 6.1 | 3.6 |
| LSD (P = .05) | 2.6 | 1.2 |

TABLE 21

Comparison of green flag leaf thickness (mm) of 'HB-128' and Kentucky and Texas bluegrass cultivars planted in nursery #3.

| Variety | Growing Season |
|---|---|
| 'HB-128' | 0.197 |
| 'HB-129' | 0.180 |
| 'HB-130' | 0.183 |
| 'HB-328' | 0.197 |
| 'HB-329' | 0.217 |
| 'Geronimo' | 0.193 |
| 'TX51-90' | 0.243 |
| 'TX49-90' | 0.247 |
| 'Ascot' | 0.193 |
| 'Reveille' | 0.210 |
| 'Kelly' | 0.198 |
| LSD (P = .05) | 0.040 |

TABLE 22

Comparison of dried flag leaf thickness (mm) of 'HB-128' and Kentucky and Texas bluegrass planted in nursery #2.

| Variety | Growing Season |
|---|---|
| 'HB-128' | 0.01689 |
| 'HB-129' | 0.01491 |
| 'HB-130' | 0.01452 |
| 'HB-328' | 0.02015 |
| 'HB 329' | 0.01819 |
| 'Reveille' | 0.02074 |
| 'Geronimo' | 0.01637 |
| 'Ascot' | 0.01659 |
| 'Midnight' | 0.01452 |
| 'Buckingham' | 0.01896 |
| 'TX 51-91' | 0.02618 |
| 'TX 39-88' | 0.01985 |
| 'TX 49-90' | 0.02311 |
| 'Kelly' | 0.01630 |
| LSD (P = .05) | 0.0033 |

TABLE 23

Comparison of flag leaf sheath length (cm) of 'HB128' and Kentucky and Texas bluegrass cultivars planted in nursery #3.

| Variety | Growing Season #1 | Growing Season #2 |
|---|---|---|
| 'HB-128' | 12.7 | 14.1 |
| 'HB-129' | 13.2 | 15.6 |
| 'HB-130' | 13.1 | 15.5 |

TABLE 23-continued

Comparison of flag leaf sheath length (cm) of 'HB128' and Kentucky and Texas bluegrass cultivars planted in nursery #3.

| Variety | Growing Season #1 | Growing Season #2 |
|---|---|---|
| 'HB-328' | 10.9 | 15.5 |
| 'HB-329' | 10.2 | 14.2 |
| 'Geronimo' | 12.3 | 16.3 |
| 'TX51-90' | 15.0 | 17.9 |
| 'TX49-90' | 10.5 | 15.5 |
| 'Ascot' | 9.5 | 13.7 |
| 'Midnight' | 9.1 | 15.0 |
| 'Reveille' | 15.0 | 17.0 |
| 'Kelly' | 10.8 | 15.7 |
| LSD (P = .05) | 1.4 | 2.1 |

TABLE 24

Flag leaf sheath length (cm) of 'HB-128' and Kentucky and Texas bluegrass cultivars planted in nursery #2.

| Variety | Growing Season |
|---|---|
| 'HB-128' | 13.7 |
| 'HB-129' | 15.5 |
| 'HB-130' | 15.3 |
| 'HB-328' | 13.1 |
| 'HB 329' | 12.9 |
| 'Reveille' | 16.4 |
| 'Geronimo' | 15.3 |
| 'Ascot' | 13.3 |
| 'Midnight' | 11.2 |
| 'Buckingham' | 14.0 |
| 'TX 51-91' | 11.4 |
| 'TX 39-88' | 14.9 |
| 'TX 49-90' | 14.8 |
| 'Kelly' | 14.4 |
| LSD (P = .05) | 2.6 |

TABLE 25

Comparison of hairs on flag leaf sheath margin of 'HB-128' and Kentucky and Texas bluegrass cultivars planted in nursery #3. (1 = Absent or 2 = Present).

| Variety | Growing Season #1 | Growing Season #2 |
|---|---|---|
| 'HB-128' | 1.0 | 1.20 |
| 'HB-129' | 1.0 | 1.10 |
| 'HB-130' | 1.0 | 1.13 |
| 'HB-328' | 1.0 | 1.30 |
| 'HB-329' | 1.0 | 1.13 |
| 'Geronimo' | 1.0 | 1.20 |
| 'TX51-90' | 1.0 | 1.00 |
| 'TX49-90' | 1.0 | 1.00 |
| 'Ascot' | 1.0 | 1.32 |
| 'Midnight' | 1.0 | n/a |
| 'Reveille' | 1.0 | 1.00 |
| 'Kelly' | 1.0 | 1.72 |
| LSD (P = .05) | 0.1 | 0.25 |

TABLE 26

Comparison of margin roughness of flag leaf sheath of 'HB128' and Kentucky and Texas bluegrass cultivars planted in nursery #3 (1 = Smooth or 2 = Rough).

| Variety | Growing Season #1 | Growing Season #2 |
|---|---|---|
| 'HB-128' | 1.5 | 1.0 |
| 'HB-129' | 1.7 | 1.0 |

TABLE 26-continued

Comparison of margin roughness of flag leaf sheath of 'HB128' and Kentucky and Texas bluegrass cultivars planted in nursery #3 (1 = Smooth or 2 = Rough).

| Variety | Growing Season #1 | Growing Season #2 |
|---|---|---|
| 'HB-130' | 1.7 | 1.0 |
| 'HB-328' | 1.6 | 1.0 |
| 'HB-329' | 1.5 | 1.0 |
| 'Geronimo' | 1.7 | 1.0 |
| 'TX51-90' | 1.3 | 1.0 |
| 'TX49-90' | 1.4 | 1.1 |
| 'Ascot' | 1.7 | 1.0 |
| 'Midnight' | 1.7 | n/a |
| 'Reveille' | 1.3 | 1.0 |
| 'Kelly' | 1.4 | 1.0 |
| LSD (P = .05) | 0.33 | 0.11 |

TABLE 27

Comparison of surface roughness of leaf sheath of 'HB-128' and Kentucky and Texas bluegrass cultivars planted in nursery #3 (1 = Smooth or 2 = Rough).

| Variety | Growing Season #1 | Growing Season #2 |
|---|---|---|
| 'HB-128' | 1.5 | 1.00 |
| 'HB-129' | 1.6 | 1.00 |
| 'HB-130' | 1.5 | 1.00 |
| 'HB-328' | 1.7 | 1.00 |
| 'HB-329' | 1.3 | 1.07 |
| 'Geronimo' | 1.5 | 1.00 |
| 'TX51-90' | 1.3 | 1.00 |
| 'TX49-90' | 1.4 | 1.00 |
| 'Ascot' | 1.7 | 1.00 |
| 'Midnight' | 1.5 | n/a |
| 'Reveille' | 1.1 | 1.00 |
| 'Kelly' | 1.6 | 1.00 |
| LSD (P = .05) | 0.3 | 0.1 |

TABLE 28

Comparison of leaf sheath glaucosity of 'HB-128' and Kentucky and Texas bluegrass cultivars planted in nursery #3. (1 = Glaucosity absent or 2 = Glaucosity Present)

| Variety | Growing Season |
|---|---|
| 'HB-128' | 1.2 |
| 'HB-129' | 1.4 |
| 'HB-130' | 1.1 |
| 'HB-328' | 1.2 |
| 'HB-329' | 1.5 |
| 'Geronimo' | 1.1 |
| 'TX51-90' | 1.2 |
| 'TX49-90' | 1.4 |
| 'Ascot' | 1.3 |
| 'Midnight' | 1.0 |
| 'Reveille' | 1.1 |
| 'Kelly' | 1.5 |
| LSD (p = .05) | 0.35 |

TABLE 29

Comparison of hairs on both side of collar margin of 'HB-128' and Kentucky and Texas bluegrass cultivars planted in nursery #3 (1 = hairs absent or 2 = hairs present).

| Variety | Growing Season #1 | Growing Season #2 |
|---|---|---|
| 'HB-128' | 1.0 | 1.0 |
| 'HB-129' | 1.0 | 1.0 |
| 'HB-130' | 1.0 | 1.0 |
| 'HB-328' | 1.0 | 1.2 |
| 'HB-329' | 1.0 | 1.0 |
| 'Geronimo' | 1.0 | 1.0 |
| 'TX51-90' | 1.0 | 1.0 |
| 'TX49-90' | 1.0 | 1.0 |
| 'Ascot' | 1.0 | 1.3 |
| 'Midnight' | 1.0 | n/a |
| 'Reveille' | 1.0 | 1.0 |
| 'Kelly' | 1.0 | 1.6 |
| LSD (P = .05) | 0.00 | 0.15 |

TABLE 30

Comparison of ligule length (mm) of 'HB-128' and Kentucky and Texas bluegrass cultivars planted in nursery #3.

| Variety | Growing Season |
|---|---|
| 'HB-128' | 1.9 |
| 'HB-129' | 1.7 |
| 'HB-130' | 1.8 |
| 'HB-328' | 2.0 |
| 'HB-329' | 2.0 |
| 'Geronimo' | 1.9 |
| 'TX51-90' | 2.0 |
| 'TX49-90' | 2.6 |
| 'Ascot' | 2.2 |
| 'Midnight' | n/a |
| 'Reveille' | 3.0 |
| 'Kelly' | 1.9 |
| LSD (P = .05) | 0.4 |

TABLE 31

Comparison of ligule length (mm) of 'HB-128' and Kentucky and Texas bluegrass cultivars planted in nursery #2.

| Variety | Growing Season |
|---|---|
| 'HB-128' | 1.4 |
| 'HB-129' | 1.3 |
| 'HB-130' | 1.7 |
| 'HB-328' | 2.4 |
| 'HB 329' | 2.2 |
| 'Reveille' | 2.3 |
| 'Geronimo' | 1.7 |
| 'Ascot' | 2.0 |
| 'Midnight' | 0.8 |
| 'Buckingham' | 2.4 |
| 'TX 51-91' | 1.6 |
| 'TX 39-88' | 2.7 |
| 'TX 49-90' | 2.0 |
| 'Kelly' | 2.1 |
| LSD (p = .05) | 0.7 |

TABLE 32

Comparison of hairs on ligule of 'HB-128' and Kentucky and Texas bluegrass cultivars planted in nursery #2. (9 = many hairs and 1 = none)

| Variety | Growing Season |
|---|---|
| 'HB-128' | 5.8 |
| 'HB-129' | 5.8 |
| 'HB-130' | 4.5 |
| 'HB-328' | 5.1 |
| 'HB 329' | 2.8 |
| 'Reveille' | 0.9 |
| 'Geronimo' | 7.1 |
| 'Ascot' | 5.6 |
| 'Midnight' | 3.9 |
| 'Buckingham' | 8.1 |
| 'TX 51-91' | n/a |
| 'TX 39-88' | 0.1 |
| TX 49-90' | n/a |
| 'Kelly' | 6.3 |
| LSD (P = .05) | 1.9 |

TABLE 33

Comparison of hairs on ligule of 'HB-128' and Kentucky and Texas bluegrass cultivars planted in nursery #3. (1 = hairs absent or 2 = hairs present).

| Variety | Growing Season #1 | Growing Season #2 |
|---|---|---|
| 'HB-128' | 1.0 | 1.5 |
| 'HB-129' | 1.0 | 1.1 |
| 'HB-130' | 1.0 | 1.2 |
| 'HB-328' | 1.0 | 1.2 |
| 'HB-329' | 1.0 | 1.1 |
| 'Geronimo' | 1.0 | 1.3 |
| 'TX51-90' | 1.0 | 1.0 |
| 'TX49-90' | 1.0 | 1.0 |
| 'Ascot' | 1.0 | 1.5 |
| 'Midnight' | 1.0 | n/a |
| 'Reveille' | 1.0 | 1.0 |
| 'Kelly' | 1.0 | 1.8 |
| LSD (P = .05) | 0.00 | 0.37 |

TABLE 34

Comparison of panicle length (cm) of 'HB-128' and Kentucky and Texas bluegrass cultivars planted in nursery #3.

| Variety | Growing Season #1 | Growing Season #2 |
|---|---|---|
| 'HB-128' | 9.9 | 10.2 |
| 'HB-129' | 9.8 | 10.2 |
| 'HB-130' | 9.7 | 11.3 |
| 'HB-328' | 8.7 | 11.9 |
| 'HB-329' | 7.6 | 10.1 |
| 'Geronimo' | 10.0 | 10.8 |
| 'TX51-90' | 12.6 | 14.7 |
| 'TX49-90' | 8.6 | 11.9 |
| 'Ascot' | 7.8 | 9.2 |
| 'Midnight' | 8.2 | 11.4 |
| 'Reveille' | 11.9 | 14.3 |
| 'Kelly' | 8.1 | 10.7 |
| LSD (P = .05) | 1.1 | 1.8 |

TABLE 35

Comparison of panicle width (cm) of 'HB-128' and Kentucky and Texas bluegrass cultivars planted in nursery #3.

| Variety | Growing Season #1 | Growing Season #2 |
|---|---|---|
| 'HB-128' | 10.4 | 10.2 |
| 'HB-129' | 9.9 | 10.2 |
| 'HB-130' | 10.3 | 10.7 |
| 'HB-328' | 8.7 | 11.1 |
| 'HB-329' | 7.7 | 9.3 |
| 'Geronimo' | 10.S | 10.4 |
| 'TXS1-90' | 10.6 | 10.3 |
| 'TX49-90' | 7.0 | 8.4 |
| 'Ascot' | 7.1 | 9.1 |
| 'Midnight' | 7.9 | 11.0 |
| 'Reveille' | 10.0 | 10.5 |
| 'Kelly' | 8.3 | 11.0 |
| LSD (p = .05) | 1.3 | 1.5 |

TABLE 36

Comparison of panicle length and width of 'HB-128' and Kentucky and Texas bluegrass cultivars planted in nursery #2.

| Variety | Panicle Length (cm) | Panicle Width (cm) |
|---|---|---|
| 'HB-128' | 12.2 | 9.8 |
| 'HB-129' | 10.5 | 10.3 |
| 'HB-130' | 10.7 | 10.8 |
| 'HB-328' | 10.7 | 9.7 |
| 'HB 329' | 8.8 | 7.9 |
| 'Reveille' | 10.9 | 9.1 |
| Geronimo' | 11.1 | 11.4 |
| 'Ascot' | 9.3 | 8.9 |
| 'Midnight' | 7.8 | 7.9 |
| 'Buckingham' | 11.5 | 10.3 |
| 'TX 51-91' | 9.7 | 8.8 |
| 'TX 39-88' | 10.7 | 8.5 |
| TX 49-90' | 8.7 | 6.8 |
| 'Kelly' | 9.8 | 9.4 |
| LSD (P = .05) | 2.3 | 1.8 |

TABLE 37

Comparison of panicle length and width of 'HB-128' and Kentucky and Texas bluegrass cultivars planted in nursery #1.

| Variety | Panicle Length (cm) | Panicle Width (cm) |
|---|---|---|
| 'HB-128' | 8.9 | 7.9 |
| 'HB-129' | 9.2 | 8.4 |
| 'HB-130' | 9.3 | 8.5 |
| 'Abbey' | 12.5 | 6.9 |
| 'HB 329' | 8.6 | 6.9 |
| 'Ascot' | 7.6 | 7.0 |
| 'Geronimo' | 8.9 | 8.1 |
| 'TX 19-88' | 13.1 | 9.7 |
| 'TX 46-90' | 13.5 | 9.5 |
| TX 4-88' | 13.7 | 9.2 |
| LSD (P = .05) | 2.7 | 1.2 |

TABLE 38

Comparison of panicle habit of 'HS-128' and Kentucky and Texas bluegrass cultivars planted in nursery #3. (1 = Nodding or 2 = Upright).

| Variety | Growing Season |
|---|---|
| 'HS-128' | 1.0 |
| 'HS-129' | 1.1 |

TABLE 38-continued

Comparison of panicle habit of 'HS-128' and Kentucky and Texas bluegrass cultivars planted in nursery #3. (1 = Nodding or 2 = Upright).

| Variety | Growing Season |
|---|---|
| 'HS-130' | 1.1 |
| 'HS-328' | 1.2 |
| 'HS-329' | 1.4 |
| 'Geronimo' | 1.1 |
| 'TX51-90' | 1.3 |
| 'TX49-90' | 1.9 |
| 'Ascot' | 1.2 |
| 'Midnight' | 1.1 |
| 'Reveille' | 1.9 |
| 'Kelly' | 1.5 |
| LSD (P = .05) | 0.4 |

TABLE 39

Comparison of panicle color of 'HB-128' and Kentucky and Texas bluegrass cultivars planted in nursery #3. (1 = not red or 2 = red).

| Variety | Growing Season |
|---|---|
| 'HB-128' | 1.0 |
| 'HB-129' | 1.0 |
| 'HB-130' | 1.0 |
| 'HB-328' | 1.0 |
| 'HB-329' | 1.1 |
| 'Geronimo' | 1.0 |
| 'TXS1-90' | 1.2 |
| 'TX49-90' | 1.1 |
| 'Ascot' | 1.1 |
| 'Midnight' | 1.0 |
| 'Reveille' | 1.0 |
| 'Kelly' | 1.0 |
| LSD (P = .05) | 0.2 |

The 'HB-128' panicle color is described by rating panicle color either as an expression absence or presence of a shade of red. A rating of 1=no expression of any shade of red on the panicle. A rating of 2=an expression a visual shade of red on the panicle when the plant is at or near the 50% flowering stage. This rating system is described in form ST-470(02-06) of Plant Variety Protection Office for Kentucky bluegrass.

TABLE 40

Comparison of panicle shape of 'HB-128' and Kentucky and Texas bluegrass cultivars planted in nursery #2.

| Variety | % Open | % Intermediate | % Compact |
|---|---|---|---|
| 'HB-128' | 98.3 | 1.6 | 0.0 |
| 'HB-129' | 96.8 | 3.2 | 0.0 |
| 'HB-130' | 100.0 | 0.0 | 0.0 |
| 'HB-328' | 98.3 | 1.6 | 0.0 |
| 'HB 329' | 94.4 | 5.6 | 0.0 |
| 'Reveille' | 27.0 | 59.8 | 13.1 |
| Geronimo' | 100.0 | 0.0 | 0.0 |
| 'Ascot' | 98.3 | 1.6 | 0.0 |
| 'Midnight' | 100.0 | 0.0 | 0.0 |
| 'Buckingham' | 100.0 | 0.0 | 0.0 |
| 'TX 51-91' | 1.8 | 23.2 | 74.9 |
| 'TX 39-88' | 1.8 | 13.5 | 84.5 |
| TX 49-90' | 1.8 | 23.9 | 74.2 |
| 'Kelly' | 98.4 | 1.6 | 0.0 |
| LSD (P = .05) | 12.8 | 15.3 | 10.1 |

TABLE 41

Comparison of panicle type of 'HB-12B' and Kentucky and Texas bluegrass cultivars planted in nursery #3. (1 = open, 2 = intermediate, or 3 = compact panicle).

| Variety | Growing Season |
|---|---|
| 'HB-12B' | 1.0 |
| 'HB-129' | 1.0 |
| 'HB-130' | 1.0 |
| 'HB-32B' | 1.1 |
| 'HB-329' | 1.1 |
| 'Geronimo' | 1.0 |
| 'TX51-90' | 2.7 |
| 'TX49-90' | 2.9 |
| 'Ascot' | 1.0 |
| 'Midnight' | 1.0 |
| 'Reveille' | 2.8 |
| 'Kelly' | 1.0 |
| LSD (p = .05) | 0.2 |

TABLE 42

Comparison of peduncle length (cm) of 'HB-128' and Kentucky and Texas bluegrass cultivars planted in nursery #3.

| Variety | Growing Season #1 | Growing Season #2 |
|---|---|---|
| 'HB-128' | 33.1 | 27.6 |
| 'HB-129' | 32.7 | 28.8 |
| 'HB-130' | 32.2 | 28.7 |
| 'HB-328' | 24.4 | 30.0 |
| 'HB-329' | 19.9 | 29.1 |
| 'Geronimo' | 29.0 | 25.6 |
| 'TX51-90' | 36.9 | 43.6 |
| 'TX49-90' | 34.4 | 46.0 |
| 'Ascot' | 24.3 | 29.7 |
| 'Midnight' | 27.4 | 24.0 |
| 'Reveille' | 37.8 | 37.3 |
| 'Kelly' | 26.4 | 27.7 |
| LSD (P = .05) | 3.8 | 4.4 |

TABLE 44

Comparison of panicle branch attitude of 'HB-128' and Kentucky and Texas bluegrass cultivars planted in nursery #3. (1 = drooping, 2 = horizontal, 3 = ascending branch attitude)

| Variety | Growing Season |
|---|---|
| 'HB-128' | 2.0 |
| 'HB-129' | 1.9 |
| 'HB-130' | 2.0 |
| 'HB-328' | 2.0 |
| 'HB-329' | 2.0 |
| 'Geronimo' | 1.8 |
| 'TXS1-90' | 2.7 |
| 'TX49-90' | 2.9 |
| 'Ascot' | 1.9 |
| 'Midnight' | 2.0 |
| 'Reveille' | 3.0 |
| 'Kelly' | 2.3 |
| LSD (P = .05) | 0.4 |

TABLE 45

Comparison of visual estimate of the amount of cotton webbing at base of lemma and on lemma nerves, after hand rubbing of panicles prior to seed conditioning of 'HB-128' and Kentucky and Texas bluegrass planted in nursery #3. (9 = most cotton webbing, 1 = no cotton webbing).

| Variety | Growing Season |
|---|---|
| 'HB-128' | 3.7 |
| 'HB-129' | 3.3 |
| 'HB-130' | 2.8 |
| 'HB-328' | 4.7 |
| 'HB-329' | 7.7 |
| 'Geronimo' | 2.8 |
| 'TX51-90' | 8.0 |
| 'TX49-90' | 6.5 |
| 'Ascot' | 3.7 |
| 'Midnight' | 2.8 |
| 'Reveille' | 7.3 |
| 'Kelly' | 4.3 |
| LSD (P = .05) | 1.0 |

TABLE 46

Comparison of the number of whorls in the panicles of 'HB-128' and Kentucky and Texas bluegrass cultivars planted in nursery #2.

| Variety | Growing Season |
|---|---|
| 'HB-128' | 8.0 |
| 'HB-129' | 8.0 |
| 'HB-130' | 8.2 |
| 'HB-328' | 8.8 |
| 'HB 329' | 8.1 |
| 'Reveille' | 7.6 |
| Geronimo' | 8.4 |
| 'Ascot' | 7.2 |
| 'Midnight' | 7.2 |
| 'Buckingham' | 8.4 |
| 'TX 51-91' | 7.0 |
| 'TX 39-88' | 7.0 |
| TX 49-90' | 7.7 |
| 'Kelly' | 8.2 |
| LSD (p = .05) | 1.3 |

TABLE 47

Comparison of the number whorls in the panicles of 'HB-128' and Kentucky and Texas bluegrass cultivars planted in nursery #1.

| Variety | Growing Season |
|---|---|
| 'HB-128' | 9.1 |
| 'HB-129' | 8.6 |
| 'HB-130' | 8.9 |
| 'Abbey' | 9.3 |
| 'HB 329' | 8.1 |
| 'Ascot' | 7.0 |
| 'Geronimo' | 8.9 |
| 'TX 19-88' | n/a |
| 'TX 46-90' | 10.0 |
| TX 4-88' | 10.0 |
| LSD (P = .05) | 0.5 |

TABLE 48

Comparison of the number of branches in the lowest whorl of the panicle of 'HB-128' and Kentucky and Texas bluegrass cultivars planted in nursery #3.

| Variety | Growing Season #1 | Growing Season #2 |
|---|---|---|
| 'HB-128' | 4.3 | 4.4 |
| 'HB-129' | 4.4 | 4.4 |
| 'HB-130' | 4.5 | 4.6 |
| 'HB-328' | 4.3 | 4.9 |
| 'HB-329' | 3.8 | 4.3 |
| 'Geronimo' | 4.5 | 4.6 |
| 'TX51-90' | 4.7 | 5.9 |
| 'TX49-90' | 3.8 | 6.0 |
| 'Ascot' | 2.7 | 4.6 |
| 'Midnight' | 3.8 | 4.7 |
| 'Reveille' | 6.4 | 7.3 |
| 'Kelly' | 4.5 | 5.2 |
| LSD (P = .05) | 1.0 | 0.8 |

TABLE 49

Comparison of the number of branches in the third whorl of the panicle of 'HB-128' and Kentucky and Texas bluegrass cultivars planted in nursery #3.

| Variety | Growing Season #1 | Growing Season #2 |
|---|---|---|
| 'HB-128' | 3.5 | 3.9 |
| 'HB-129' | 3.5 | 3.8 |
| 'HB-130' | 4.6 | 4.1 |
| 'HB-328' | 3.3 | 4.2 |
| 'HB-329' | 2.7 | 3.7 |
| 'Geronimo' | 3.6 | 3.9 |
| 'TX51-90' | 4.2 | 5.6 |
| 'TX49-90' | 3.3 | 5.7 |
| 'Ascot' | 3.1 | 4.2 |
| 'Midnight' | 3.33 | 3.9 |
| 'Reveille' | 5.3 | 5.5 |
| 'Kelly' | 4.0 | 4.2 |
| LSD (P = .05) | 0.8 | 0.5 |

TABLE 50

Comparison of the number of branches in the first and third whorl of the panicle of 'HB-128' and Kentucky and Texas bluegrass cultivars planted in nursery #1.

| Variety | First Whorl | Third Whorl |
|---|---|---|
| 'HB-128' | 4.1 | 3.3 |
| 'HB-129' | 4.0 | 3.3 |
| 'HB-130' | 3.9 | 3.2 |
| 'Abbey' | 3.1 | 3.1 |
| 'HB 329' | 4.4 | 3.8 |
| 'Ascot' | 2.8 | 2.4 |
| 'Geronimo' | 4.0 | 3.5 |
| 'TX 19-88' | 5.4 | n/a |
| 'TX 46-90' | 4.9 | 4.9 |
| TX 4-88' | 5.7 | 6.4 |
| LSD (p = .05) | 0.8 | 0.8 |

TABLE 51

Comparison of the number of branches in the first and third whorl of the panicle of 'HB-128' and Kentucky and Texas bluegrass cultivars planted in nursery #2.

| Variety | First Whorl | Third Whorl |
|---|---|---|
| 'HB-128' | 4.2 | 3.3 |
| 'HB-129' | 4.0 | 3.2 |
| 'HB-130' | 4.3 | 3.3 |
| 'HB-328' | 4.3 | 2.9 |
| 'HB 329' | 3.6 | 2.1 |
| 'Reveille' | 5.2 | 3.2 |
| Geronimo' | 4.4 | 3.1 |
| 'Ascot' | 3.8 | 2.2 |
| 'Midnight' | 4.1 | 2.5 |
| 'Buckingham' | 3.2 | 2.3 |
| 'TX 51-91' | 4.3 | 2.9 |
| 'TX 39-88' | 2.3 | 2.8 |
| TX 49-90' | 3.6 | 3.2 |
| 'Kelly' | 4.6 | 3.1 |
| LSD (P = .05) | 0.9 | 1.1 |

TABLE 52

Comparison of spikelet length (mm) in the first and third whorl of panicle of 'HB 128' and Kentucky and Texas bluegrass cultivars planted in nursery #2.

| Variety | First Whorl | Third Whorl |
|---|---|---|
| 'HB-128' | 6.9 | 6.8 |
| 'HB-129' | 7.6 | 7.1 |
| 'HB-130' | 6.4 | 6.7 |
| 'HB-328' | 6.6 | 6.8 |
| 'HB 329' | 6.2 | 6.5 |
| 'Reveille' | 6.1 | 6.4 |
| Geronimo' | 5.5 | 6.3 |
| 'Ascot' | 5.6 | 5.8 |
| 'Midnight' | 5.6 | 6.3 |
| 'Buckingham' | 6.9 | 6.9 |
| 'TX 51-91' | 7.5 | 7.4 |
| 'TX 39-88' | 8.6 | 8.5 |
| TX 49-90' | 9.7 | 9.7 |
| 'Kelly' | 6.3 | 6.1 |
| LSD (P = .05) | 1.7 | 1.7 |

TABLE 53

Comparison of the spikelet width (mm) in first and third whorl of the panicle of 'HB-128' and Kentucky and Texas bluegrass cultivars planted in nursery #2.

| Variety | First Whorl | Third Whorl |
|---|---|---|
| 'HB-128' | 3.8 | 4.0 |
| 'HB-129' | 4.5 | 4.0 |
| 'HB-130' | 4.2 | 3.6 |
| 'HB-328' | 5.2 | 4.4 |
| 'HB 329' | 4.3 | 3.8 |
| 'Reveille' | 4.0 | 4.2 |
| Geronimo' | 4.2 | 4.0 |
| 'Ascot' | 4.4 | 4.3 |
| 'Midnight' | 2.5 | 3.0 |
| 'Buckingham' | 4.6 | 4.7 |
| 'TX 51-91' | 7.1 | 6.9 |
| 'TX 39-88' | 5.9 | 5.7 |
| TX 49-90' | 8.2 | 8.0 |
| 'Kelly' | 4.4 | 4.3 |
| LSD (P = .05) | 1.9 | 1.6 |

TABLE 54

Comparison of the length (mm) of the glume #1 in the first and third whorl of 'HB-128' and Kentucky and Texas bluegrass cultivars planted in nursery #2.

| Variety | #1 Glume Length in First Whorl (mm) | #1 Glume Length in Third Whorl (mm) |
|---|---|---|
| 'HB-128' | 3.1 | 2.9 |
| 'HB-129' | 3.1 | 3.2 |
| 'HB-130' | 3.0 | 3.0 |
| 'HB-328' | 3.4 | 3.6 |
| 'HB 329' | 3.7 | 3.6 |
| 'Reveille' | 2.9 | 3.3 |
| Geronimo' | 2.7 | 3.0 |
| 'Ascot' | 2.9 | 2.9 |
| 'Midnight' | 2.6 | 2.5 |
| 'Buckingham' | 3.1 | 3.0 |
| 'TX 51-91' | 3.5 | 3.2 |
| 'TX 39-88' | 3.6 | 3.6 |
| TX 49-90' | 5.4 | 5.0 |
| 'Kelly' | 2.8 | 2.9 |
| LSD (p = .05) | 0.9 | 0.7 |

TABLE 55

Comparison of the length (mm) of glume #2 in first and third whorl of 'HB-128' and Kentucky and Texas bluegrass cultivars planted in nursery #2.

| Variety | Glume Length in First Whorl (mm) | Glume Length in Third Whorl (mm) |
|---|---|---|
| 'HB-128' | 3.3 | 3.1 |
| 'HB-129' | 3.5 | 3.3 |
| 'HB-130' | 3.0 | 3.2 |
| 'HB-328' | 3.8 | 3.9 |
| 'HB 329' | 3.6 | 3.7 |
| 'Reveille' | 3.3 | 3.5 |
| Geronimo' | 2.9 | 3.1 |
| 'Ascot' | 3.1 | 3.2 |
| 'Midnight' | 3.1 | 3.3 |
| 'Buckingham' | 3.4 | 3.4 |
| 'TX 51-91' | 4.2 | 4.3 |
| 'TX 39-88' | 4.0 | 4.2 |
| TX 49-90' | 6.0 | 5.4 |
| 'Kelly' | 3.0 | 3.0 |
| LSD (P = .05) | 1.0 | 0.8 |

TABLE 56

Comparison of the number of florets per spikelet in first and third whorl in panicles of 'HB-128' and Kentucky and Texas bluegrass cultivars planted in nursery #2.

| Variety | Florets per Spikelet In First Whorl | Florets per Spikelet In Third Whorl |
|---|---|---|
| 'HB-128' | 6.7 | 6.3 |
| 'HB-129' | 8.6 | 7.0 |
| 'HB-130' | 6.3 | 6.4 |
| 'HB-328' | 5.2 | 5.0 |
| 'HB 329' | 4.6 | 5.0 |
| 'Reveille' | 4.0 | 4.9 |
| Geronimo' | 5.2 | 6.0 |
| 'Ascot' | 3.8 | 4.3 |
| 'Midnight' | 4.3 | 5.6 |
| 'Buckingham' | 6.7 | 7.1 |
| 'TX 51-91' | 8.8 | 8.3 |
| 'TX 39-88' | 8.0 | 7.9 |
| TX 49-90' | 8.7 | 8.6 |
| 'Kelly' | 4.3 | 4.9 |
| LSD (P = .05) | 1.7 | 1.8 |

TABLE 57

Comparison of the length and width (mm) of 10 seeds of 'HB-128' and Kentucky and Texas bluegrass cultivars planted in nursery #3.

| Variety | Length 10 Seeds (mm) | Width of 10 Seeds (mm) |
|---|---|---|
| 'HB-128' | 32.0 | 9.9 |
| 'HB-129' | 32.8 | 9.8 |
| 'HB-130' | 31.9 | 9.5 |
| 'HB-328' | 31.3 | 10.3 |
| 'HB-329' | 38.2 | 11.0 |
| 'Geronimo' | 32.5 | 10.8 |
| 'TX51-90' | n/a | n/a |
| 'TX49-90' | n/a | n/a |
| 'Ascot' | 32.2 | 9.8 |
| 'Midnight' | 33.0 | 9.3 |
| 'Reveille' | 32.5 | 10.8 |
| 'Kelly' | 32.8 | 10.1 |
| LSD (P = .05) | 2.5 | 1.0 |

TABLE 58

Comparison of 1000 count seed weight (grams) of 'HB-128' and Kentucky and Texas bluegrass cultivars planted in nursery #3.

| Variety | 1000 count seed weight (grams) |
|---|---|
| 'HB-128' | 0.5680 |
| 'HB-129' | 0.5682 |
| 'HB-130' | 0.5735 |
| 'HB-328' | 0.5411 |
| 'HB-329' | 0.5881 |
| 'Geronimo' | 0.5760 |
| 'TX51-90' | n/a |
| 'TX49-90' | n/a |
| 'Ascot' | 0.5695 |
| 'Midnight' | 0.5217 |
| 'Reveille' | 0.6020 |
| 'Kelly' | 0.5729 |
| LSD (P = .05) | 0.0791 |

TABLE 59

Comparison of summer re-growth during an extended 8 week drought period following harvest of 'HB-128' and Kentucky and Texas bluegrass cultivars planted in nursery #3.

| Variety | Green Tissue (%) |
|---|---|
| 'HB-128' | 36.7 |
| 'HB-129' | 28.3 |
| 'HB-130' | 38.3 |
| 'HB-328' | 16.7 |
| 'HB-329' | 60.0 |
| 'Geronimo' | 41.7 |
| 'TX51-90' | 86.7 |
| 'TX49-90' | 90.0 |
| 'Ascot' | 16.7 |
| 'Midnight' | 10.0 |
| 'Reveille' | 88.3 |
| 'Kelly' | 10.0 |
| LSD (p = .05) | 15.2 |

* This table shows that 'HB 128' has a more rapid regrowth following an drought induced dormancy than 'HB 129'.

TABLE 60

Comparison of plant spread (aggressiveness) at 15 months after planting of 'HB-128' and Kentucky and Texas bluegrass cultivars planted in nursery #3 (when measured in mid-winter).

| Variety | Plant Spread (square cm area) |
|---|---|
| 'HB-128' | 2565 |
| 'HB-129' | 2279 |
| 'HB-130' | 2376 |
| 'HB-328' | 1520 |
| 'HB 329' | 1097 |
| 'Reveille' | 1210 |
| Geronimo' | 2178 |
| 'Ascot' | 950 |
| 'Midnight' | 912 |
| 'Buckingham' | 1330 |
| 'TX 51-91' | 672 |
| 'TX 39-88' | 385 |
| TX 49-90' | 337 |
| 'Kelly' | 982 |
| LSD (P = .05) | 544 |

TABLE 61

Comparison of incidence of rust and dollarspot disease on plot of a turf planting of 'HB-128' and Kentucky bluegrass cultivars planted in Valley Center, California (one year after seeding).

| Variety | Rust % | Dollarspot % |
|---|---|---|
| 'HB-128' | 15.3 | 13.3 |
| 'HB-129' | 16.7 | 21.7 |
| 'HB-130' | 13.3 | 16.7 |
| 'HB-328' | 2.0 | 0.0 |
| 'HB 329' | 2.0 | 0.3 |
| 'Abbey' | 13.3 | 16.7 |
| 'Midnight' | 26.7 | 0.3 |
| 'Apollo' | 23.3 | 0.0 |
| LSD (P = .05) | 10.3 | 10.6 |

* This table shows that 'HB 128' has a better tolerance to foliar dollarspot disease than 'HB 129'.

TABLE 62

Comparison of spring color and texture of 'HB-128' and Kentucky bluegrass cultivars ma turf planting in Valley Center, California (planted in October).

| Variety | Spring Color 9 = Dark Green, 1 = Yellow | Spring Texture 9 = Fine, 1 = Coarse |
|---|---|---|
| 'HB-128' | 5.3 | 6.0 |
| 'HB-129' | 5.0 | 6.7 |
| 'HB-130' | 6.0 | 6.3 |
| 'HB-328' | 8.0 | 5.3 |
| 'HB 329' | 8.0 | 5.0 |
| 'Abbey' | 5.3 | 6.3 |
| 'Midnight' | 7.0 | 7.0 |
| 'Apollo' | 7.0 | 7.0 |
| LSD (P = .05) | 1.0 | 0.8 |

TABLE 63

Comparison of summer (June) and winter (January) turf performance of 'HB-128' and Kentucky bluegrass cultivars in Valley Center, California.

| Variety | % Leaf Roll (Heat Stress) | % Winter Discolor (Cold Stress) |
|---|---|---|
| 'HB-128' | 60.0 | 41.7 |
| 'HB-129' | 43.3 | 41.7 |
| 'HB-130' | 40.0 | 43.3 |
| 'HB-328' | 0.0 | 33.3 |
| 'HB 329' | 8.3 | 33.3 |
| 'Abbey' | 36.7 | 50.0 |
| 'Midnight' | 36.7 | 20.0 |
| 'Apollo' | 36.7 | 26.7 |
| LSD (p = .05) | 34.4 | 4.9 |

TABLE 64

Comparison of vertical growth performance and greening in early spring of 'HB-128' and Kentucky bluegrass cultivars in turf planting in Gervais, Oregon (planted in September).

| Variety | Spring Vertical Growth (height - cm) | Early Spring Greenup 9 = Green, 1 = Brown |
|---|---|---|
| 'HB-128' | 91.3 | 6.7 |
| 'HB-130' | 82.3 | 6.3 |
| 'HB-328' | 70.3 | 4.7 |
| 'HB 329' | 64.3 | 4.3 |
| 'HB-129' | 84.3 | 6.0 |
| 'Bluemax' | 59.3 | 3.3 |
| 'Courtyard' | 54.0 | 2.3 |
| 'Avalanche' | 83.0 | 6.7 |
| 'Kenblue' | 92.0 | 7.3 |
| 'Geronimo' | 68.7 | 5.3 |
| LSD (P = .05) | 14.5 | 0.9 |

* This table demonstrates that 'HB 128' is quicker to greenup in springtime than 'HB 129' and shows better recovery from winter induced dormancy.

TABLE 65

Comparison of seedling density in two different turf plantings of 'HB-128' and Kentucky and Texas bluegrass cultivars fall planted (in Season #1 and #2) in Gervais, Oregon.

| Variety | Growing Season #1 21 Days After Planting | Growing Season #2 27 Days After Planting |
|---|---|---|
| 'HB-128' | 45.0 | 17.5 |
| 'HB-129' | 25.0 | 9.5 |
| 'HB-130' | 38.3 | 12.0 |
| 'HB-328' | 31.7 | 16.3 |
| 'HB-329' | 7.7 | 9.8 |
| 'Geronimo' | 35.0 | 11.5 |
| 'Midnight' | n/a | 11.3 |
| 'Reveille' | n/a | 1.1 |
| 'Ascot' | n/a | 14.5 |
| 'Apollo' | n/a | 6.8 |
| 'Kenblue' | 56.7 | 23.0 |

TABLE 65-continued

Comparison of seedling density in two different turf plantings of 'HB-128' and Kentucky and Texas bluegrass cultivars fall planted (in Season #1 and #2) in Gervais, Oregon.

| Variety | Growing Season #1 21 Days After Planting | Growing Season #2 27 Days After Planting |
|---|---|---|
| 'Park' | n/a | 30.0 |
| 'Longhorn' | n/a | 22.5 |
| LSD (P = .05) | 14.6 | 6.85 |

* This table shows that 'HB 128' has demonstrated a more rapid germination and establishment than other hybrid and some Kentucky bluegrasses.

TABLE 66

Comparison of summer turf dormancy of 'HB-128' and Kentucky bluegrass cultivars in Cleveland, Texas.

| Variety | Percent Brown Turf |
|---|---|
| 'HB-128' | 56.7 |
| 'HB-129' | 41.7 |
| 'HB-130' | 38.3 |
| 'HB-328' | 31.7 |
| 'Reveille' | 50.0 |
| 'Ascot' | 43.3 |
| 'Coventry' | 46.7 |
| 'Abbey' | 40.0 |
| LSD (p = .10) | 14.43 |

Additional Color Description

The upper and lower leaf blade surface colors of 'HB-128' were determined by comparing several actively growing leaves one at a time, in full sun, with color chips from the Munsell Book of Color, Volume I of a two volume set as a reference. On this basis, the color of the upper and lower leaf blade surfaces were determined. The upper leaf blade surfaces ranged from 5GY 4/4 to 4/6 and the lower leaf blade surfaces ranged from 5GY 3/4 to 3/6.

Additionally, color designations were determined from tillers harvested from the plant nursery using the Munsell Book of Color, Volume I of a two volume set as a reference, as follows: 10YR 7/4 to 8/6 for 'HB-228' culm; 10YR 7/4 to 7/6 for peduncle; 10YG 7/4 to 8/4 for spikelet; and 10YG 6/4 to 7/4 for 'HB-128' seed.

What is claimed is:

1. A new and distinct hybrid variety of Texas bluegrass× Kentucky bluegrass plant, as herein illustrated and described and characterized by more rapid establishment; a medium dark green, dense turf; a medium wide leaf blade; aggressive spreading growth habit; a reduced level of cotton on the seed; early spring greenup and rapid recovery from summer dormancy and a medium to high seed yield potential.

* * * * *